United States Patent
King et al.

(10) Patent No.: US 10,564,157 B2
(45) Date of Patent: Feb. 18, 2020

(54) ANALYTE DETECTION UTILIZING NANOPOROUS GLASS ANALYTE CONCENTRATOR

(71) Applicant: Corning Incorporated, Corning, NY (US)

(72) Inventors: Jeffrey Stapleton King, Menlo Park, CA (US); Prantik Mazumder, Ithaca, NY (US); Elaine Victoria Seraya, Santa Clara, CA (US)

(73) Assignee: Corning Incorporated, Corning, NY (US)

( * ) Notice: Subject to any disclaimer, the term of this patent is extended or adjusted under 35 U.S.C. 154(b) by 0 days.

(21) Appl. No.: 15/905,011

(22) Filed: Feb. 26, 2018

(65) Prior Publication Data

US 2018/0246091 A1    Aug. 30, 2018

Related U.S. Application Data

(60) Provisional application No. 62/464,739, filed on Feb. 28, 2017.

(51) Int. Cl.
   *G01N 33/552* (2006.01)
   *G01N 33/543* (2006.01)
   *G01N 33/549* (2006.01)

(52) U.S. Cl.
   CPC ........ *G01N 33/552* (2013.01); *G01N 33/549* (2013.01); *G01N 33/5436* (2013.01); *G01N 33/54366* (2013.01)

(58) Field of Classification Search
   CPC ............. G01N 33/552; G01N 33/5436; G01N 33/549; G01N 33/54366
   See application file for complete search history.

(56) References Cited

U.S. PATENT DOCUMENTS 2,106,744 A    2/1938  Hood et al.
4,052,010 A *  10/1977 Baker .................... A61K 39/44
                                                             241/20

(Continued)

FOREIGN PATENT DOCUMENTS

KR           842830 B1    7/2008
KR      2013125429 A     11/2013

OTHER PUBLICATIONS

Alverez-Herrero et al; "Adsorption of Water on Porous Vycor Glass Studied by Ellipsometry"; Applied Optics; vol. 40, No. 4; Feb. 1, 2001; pp. 527-532.

(Continued)

*Primary Examiner* — Melanie Brown
(74) *Attorney, Agent, or Firm* — Russell S. Magaziner

(57) ABSTRACT

An analyte capture device and related systems and methods are provided. The analyte capture device includes a glass material, an outer surface defined by the glass material, and a plurality of pores formed in the glass material along at least a portion of the outer surface. The analyte capture device is exposed to an environment containing an analyte for a period of time such that the analyte is captured within the plurality of pores of the glass material. The concentration of the analyte within the glass material is greater than a concentration of the analyte within the environment. The analyte capture device is then removed from the environment, and a property of the analyte within the analyte capture device is detected via an analyte detection system.

20 Claims, 8 Drawing Sheets

(56) References Cited

U.S. PATENT DOCUMENTS

| | | | |
|---|---|---|---|
| 5,589,396 A | 12/1996 | Frye et al. | |
| 6,136,170 A * | 10/2000 | Inoue | G01N 27/4065 |
| | | | 204/408 |
| 6,171,378 B1 | 1/2001 | Manginell et al. | |
| 6,274,872 B1 * | 8/2001 | Katerkamp | G01N 21/6428 |
| | | | 250/458.1 |
| 7,662,636 B2 | 2/2010 | Maruo et al. | |
| 8,366,814 B2 | 2/2013 | Jones et al. | |
| 2002/0017128 A1 * | 2/2002 | Shirai | C03C 8/24 |
| | | | 73/31.05 |
| 2002/0135771 A1 * | 9/2002 | Witty | G01N 33/558 |
| | | | 356/445 |
| 2005/0112557 A1 * | 5/2005 | Liu | G01N 33/53 |
| | | | 435/5 |
| 2007/0134748 A1 * | 6/2007 | Kudo | G01N 33/552 |
| | | | 435/7.92 |
| 2009/0042311 A1 * | 2/2009 | Thompson | G01N 21/6428 |
| | | | 436/164 |
| 2009/0234107 A1 * | 9/2009 | Murata | G01N 33/552 |
| | | | 530/391.1 |
| 2017/0292914 A1 | 10/2017 | King | |

OTHER PUBLICATIONS

Author Unknown; "A Porous Glass That Resists Chemical Attack, Short Report"; Materials Engineering, (1979) p. 92.

Bajnoczi et al; "On the Lack of Capillary Mossbauer Spectroscopic Effect for SNII-Containing Aqueous Solutions Trapped in Corning Vycor 'Thirsty' Glass"; J. Radioanal Nucl Chem (2014), 302; pp. 695-700.

Hao et al; "Measurements of NO2, SO2, O3, Benzene and Toluene Using Differential Optical Absorption Spectroscopy (DOAS) in Shanghai, China"; Annali Di Chimica, 96, 2006, p. 365-375.

Haynes et al; "Light Scattering and Capillary Condensation in Porous Media"; Journal of Colloid and Interface Science, vol. 59, No. 1, Mar. 15, 1977; pp. 24-30

Kumar et al; "Reversible SO2 Uptake by Tetraalkylammonium Halides: Energetics and Structural Aspects of Adduct Formation Between SO2 and Halide Ions"; S. Anorg. Allg. Chem., 2012, 638 (5) 744-753.

Lee et al; "Fluorescent Chemodosimeter for Selective Detection of Cyanide in Water"; Organic Letters; vol. 10, No. 1; 2008; pp. 49-51.

Marino; "Porous Glass as an Adsorbent in Thin-Layer Chromatography"; J. Chromatog., 46, (1970) pp. 125-129.

Mitropoulos et al; "On the Formation of Nanobubbles in Vycor Porous Glass During the Desorption of Halogenated Hydrocarbons"; Scientific Reports; Jun. 5, 2015; 12 Pages.

Nordberg; "Properties of Some Vycor-Brand Glasses"; Journal of the American Ceramic Society; vol. 27, No. 10, (1944) pp. 299-305.

Novak et al; "Vycor Porous Glass (Thirsty Glass) as a Reaction Medium for Optical Waveguide Based Chemical Vapor Detectors"; Spectroscopy Letters; 21:2; Jan. 3, 2007; pp. 127-145.

Perez-Quintanilla et al; "2-Mercaptothiazoline Modified Mesoporous Silica for Mercury Removal From Aqueous Media"; Journal of Hazardous Materials, B134 (2006); pp. 245-256.

Reeds et al; "Adsorption of Mixed Vapors"; Industrial and Engineering Chemistry; vol. 51, No. 5; May 959; pp. 707-709.

Schwertz; "Fluid-Flow Study of Porous Glass"; Journal of the American Ceramic Society; vol. 32, No. 12; (1949) pp. 390-393.

Standard Operating Procedures for Sulfur Dioxide (SO2) Monitoring by Ultraviolet Fluorescence; Department of Environmental Conservation Division of Air Quality; Anchorage, AK; 2012, 54 Pages.

Stiernstedt et al; "Forces Between Silica Surfaces With Adsorbed Cationic Surfactants: Influence of Salt and Added Nonionic Surfactants"; Langmuir, 2005, 21, 1875-1883.

* cited by examiner

ANALYTE DETECTION UTILIZING NANOPOROUS GLASS ANALYTE CONCENTRATOR

CROSS-REFERENCE TO RELATED APPLICATIONS

This application claims the benefit of priority of U.S. Provisional Application Ser. No. 62/464,739 filed on Feb. 28, 2017 the contents of which are relied upon and incorporated herein by reference in their entirety as if fully set forth below.

BACKGROUND

The disclosure relates generally to the field of analyte detection, and specifically to the use of porous glass as an analyte capture device. In various applications, an analyte (e.g., a pollutant in air or water, a pathogen, a biomarker, etc.) is measured or detected. In some environments, the analyte is present in the environment in very low concentrations, making detection/measurement difficult. When such a low concentration analyte is being measured, measurement may require very sensitive equipment, expense, long test times, etc.

SUMMARY

One embodiment of the disclosure relates to a method of detecting a low concentration analyte in an environment. The method includes exposing an analyte capture device to an environment containing an analyte. The analyte capture device includes a glass material, an outer surface defined by the glass material and a plurality of pores formed in the glass material along at least a portion of the outer surface such that the glass material has a porosity of at least 10%. The method includes continuing exposure of the analyte capture device to the environment for a period of time such that the analyte is captured within the plurality of pores of the glass material. A concentration of the analyte within the glass material is greater than a concentration of the analyte within the environment. The method includes removing the analyte capture device from the environment. The method includes detecting a property of the analyte captured by the analyte capture device via an analyte detection system.

An additional embodiment of the disclosure relates to an analyte detection system. The analyte detection system includes an analyte capture device. The analyte capture device includes a glass material, an outer surface defined by the glass material and a plurality of pores formed in the glass material along at least a portion of the outer surface of the glass material. The plurality of pores have an average pore width that is less than 100 nm, and the glass material captures an analyte within the plurality of pores when the analyte capture device is exposed to an environment including the analyte such that a concentration of the analyte within the glass material is greater than a concentration of the analyte in the environment. The analyte detection system includes a detection system configured to detect a property of the analyte captured by the analyte capture device.

An additional embodiment of the disclosure relates to an analyte capture device. The analyte capture device includes a sheet of glass material including a first major surface. The analyte capture device includes a porous analyte capture area located along the first major surface, and the porous area has a porosity of at least 10%. The analyte capture device includes a cover hermetically sealed around the first major surface of the sheet of glass material over the porous analyte capture area. The cover is at least one of openable or removable to expose the porous analyte capture area to an environment containing an analyte.

Additional features and advantages will be set forth in the detailed description that follows, and, in part, will be readily apparent to those skilled in the art from the description or recognized by practicing the embodiments as described in the written description and claims hereof, as well as the appended drawings.

It is to be understood that both the foregoing general description and the following detailed description are merely exemplary, and are intended to provide an overview or framework to understand the nature and character of the claims.

The accompanying drawings are included to provide a further understanding and are incorporated in and constitute a part of this specification. The drawings illustrate one or more embodiment(s), and together with the description serve to explain principles and the operation of the various embodiments.

DETAILED DESCRIPTION

Referring generally to the figures, methods and systems for detecting an analyte present in an environment are shown. In general, the methods and systems discussed herein use an analyte capture device formed from a porous glass article that absorbs an analyte in the environment. The analyte captured by the glass article is then detected using one or more detection systems or techniques (e.g., transmission spectroscopy, fluorescence spectroscopy, adsorption spectroscopy, thermal desorption spectroscopy, mass spectroscopy, inductively coupled plasma mass spectrometry, etc.).

In particular embodiments, the analyte capture device may be used to detect an analyte that is present in low concentrations in the environment for a period of time such that a relatively large concentration of the analyte is captured by the glass analyte capture device. The concentrated analyte captured by the analyte capture device is then measured using one of the detection systems noted above. Applicant believes that the embodiments discussed herein may provide for more accurate analyte reading or use of less sensitive analyte detection equipment by concentrating the analyte from the environment within the analyte capture device and then reading the concentrated analyte from the analyte capture device. Thus, Applicant believes that utilizing the analyte capture device discussed herein may allow better analyte detection using less sensitive (and less expensive) detection systems. Specifically, in some embodiments, the high concentration of analyte provided by the device discussed herein obviates the need for optical or electrical amplification of the interrogation signals, which in turn may allow for the use of lower cost instrumentation, relaxing the needs for precision, accuracy, and signal-to-noise performance of the detection system.

In addition, the glass analyte capture device is believed to provide a useful substrate for supporting a variety of additional analyte capture materials within the pores of the glass of the analyte capture device. The additional analyte capture material may be a variety of materials that provide for increased or differential capture of a desired analyte from the environment. Thus, in various embodiments, the porous glass analyte capture device discussed herein is customized or targeted to capture one or more target analyte based on the type of analyte capture material that is supported within the pores of the analyte capture device.

Figure 1A:
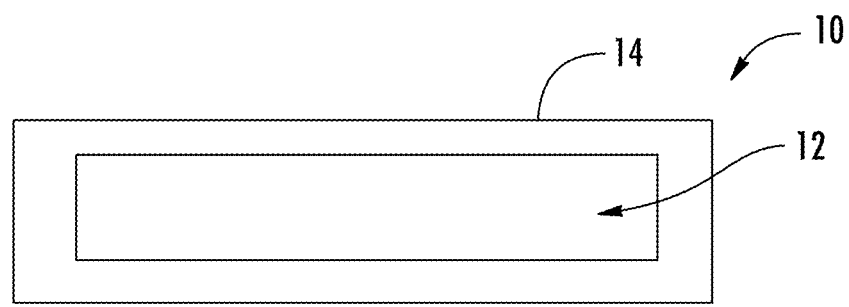
FIGS. 1A-1D show a system and method for detecting a low concentration analyte in an environment using a glass analyte capture device, according to an exemplary embodiment.

Referring to FIGS. 1A-1D, a method and system of detecting an analyte in an environment is shown according to an exemplary embodiment. FIG. 1A shows an analyte capture device 10. In general, analyte capture device 10 is formed from a porous glass material (such as glass sheet 60 shown in FIGS. 2-4). In such embodiments, the glass material of analyte capture device 10 includes an outer surface 12 and a plurality of pores located in the glass material. As shown in FIG. 1A, outer surface 12 may be a substantially planar surface. In some embodiments, the pores are located along at least a portion of outer surface 12. In some embodiments, the glass material of analyte capture device 10 is a completely porous material and the pores are evenly distributed through the glass material. In other embodiments, the pores are located along all of outer surface 12, and in yet other embodiments, the pores may be located only within a particular portion of the glass material of analyte capture device or along only a portion of outer surface 12.

In the specific embodiment shown, analyte capture device 10 includes a seal structure or cover 14. In general, cover 14 blocks some or all of the pores of the glass material of analyte capture device 10 from being exposed to the environment and analyte until analyte capture device 10 is to be used. In such embodiments, cover 14 forms a hermetic seal around all or a portion of analyte capture device 10. Thus, cover 14 prevents potential contamination of analyte capture device 10 prior to use. In one embodiment, analyte capture device 10 may be subject to pre-test thermal cycling to remove/destroy contaminants that may have been absorbed into the glass material of analyte capture device 10 prior to use.

Figure 1B:
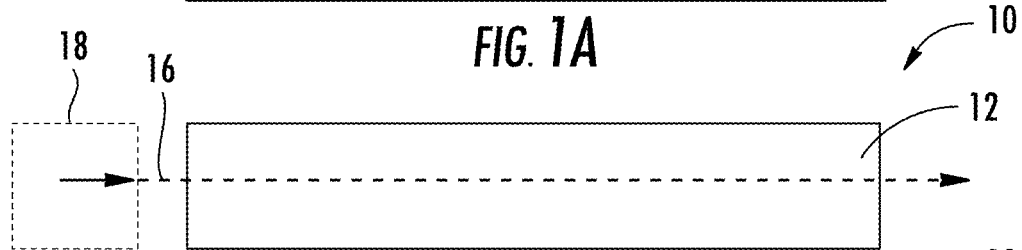

As shown in FIG. 1B, analyte capture device is exposed to an environment containing an analyte. In general, FIG. 1B shows an analyte containing fluid 16 from the environment moving across outer surface 12 such that the pores of analyte capture device 10 are exposed to the desired analyte. In specific embodiments, cover 14 is removed such that the pores of analyte capture device 10 may be exposed to fluid 16.

In general, analyte containing fluid 16 and the environment including fluid 16 may be any material or environment that contains a desired analyte. By way of example, analyte capture device 10 may be used to capture various chemical compositions, contaminants, chemicals, pathogens, etc. In specific embodiments, the environment may be a water source, a body of water, air, outdoor air, indoor air, organic solvents, etc., and the analyte may be a specific chemical or element, an environmental contaminant, a pathogen, etc. present in the environment. In specific embodiments, analyte capture device 10 can be used to monitor outdoor air pollution, indoor air quality, water contamination, cleanroom air, automotive interiors, etc. In some embodiments, the environment may be a human or animal and the fluid may be a bodily fluid or material that contains a desired analyte, such as a particular protein, a pathogen, glucose, a fat, cholesterol, a hormone, nucleic acid, etc.

In a specific embodiment, analyte capture device 10 may be used in conjunction with an exposure control device 18. Exposure control device 18 may be one of a variety of devices that meters, measures and/or controls the volume, rate, etc. of fluid 16 that analyte capture device 10 is exposed to. In some embodiments, exposure control device 18 may be used in applications where analyte concentration in the environment (e.g., a body of water, atmospheric air, etc.) are low enough that exposing analyte capture device 10 to a sample from the test environment will not contain enough analyte for detection. In such embodiments, exposure control device 18 provides a continuous exposure of analyte capture device 10 to the environmental fluid (e.g., air or water) allowing enough analyte to be captured for detection.

In some anticipated embodiments, exposure control device 18 may be used in applications where precise quantification of the amount of an analyte present in an environment is desired by allowing a measured amount of analyte within analyte capture device 10 to be correlated to the amount (e.g., volume) of fluid 16 that analyte capture device 10 was exposed to. In various embodiments, exposure control device 18 includes a component for measuring the amount fluid 16 that analyte capture device 10 was exposed to, such as a flow meter.

In some embodiments, exposure control device 18 includes a component for moving fluid 16 across surface 12 of analyte capture device. In such embodiments, the component of exposure control device 18 for moving fluid 16 includes a pump, a microfluidic pump, a fan, etc., that moves fluid 16 at a predetermined rate or at a measurable rate across surface 12.

In specific embodiments in which quantification of the analyte is desired, exposure control device 18 provides precise control and monitoring of the time and flow rate of analyte containing fluid 16. In such embodiments, exposure control device 18 includes a gas or liquid pumping and distribution system. As one example, for small liquid volumes, exposure control device 18 includes a microfluidic pump to deliver a well-controlled amount of the liquid material to porous surface 12 of the glass material of analyte capture device 10. The actual concentration of the analyte in the environment can be calculated based on the volume of liquid delivered to surface 12 of analyte capture device 10 and on exposure time. In some embodiments, the pumping system of exposure control device 18 may also be used to flush out the pores of analyte capture device 10 after measurements are complete. In embodiments where fluid stream 16 is a gas, exposure control device 18 may configured to move hot air/inert gas through itself to desorb trapped analytes.

Figure 1C:
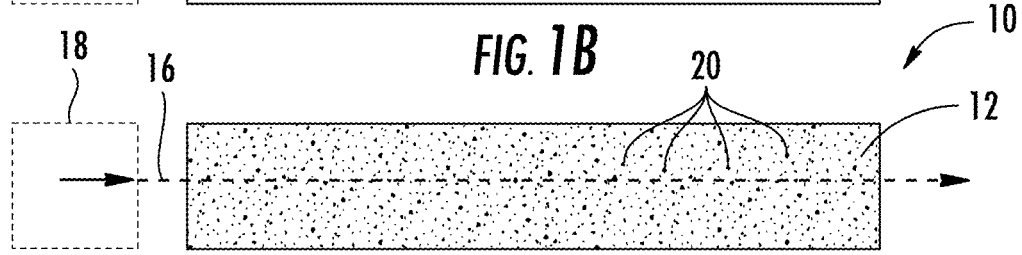

Referring to FIG. 1C, exposure of analyte capture device 10 to fluid 16 (and to the analyte contained therein) is continued for a period of time allowing an analyte 20 to become captured within the glass material of analyte capture device 10. As fluid 16 continues to come into contact with analyte capture device 10, analyte 20 continually becomes absorbed, trapped, bonded, etc. or otherwise captured within the pores of the glass material of analyte capture device 10. Analyte capture device 10 is exposed to fluid 16 and the environment for sufficient time to allow analyte 20 to become concentrated within analyte capture device 10 at a concentration level higher than the concentration level in the environment.

Figure 1D:
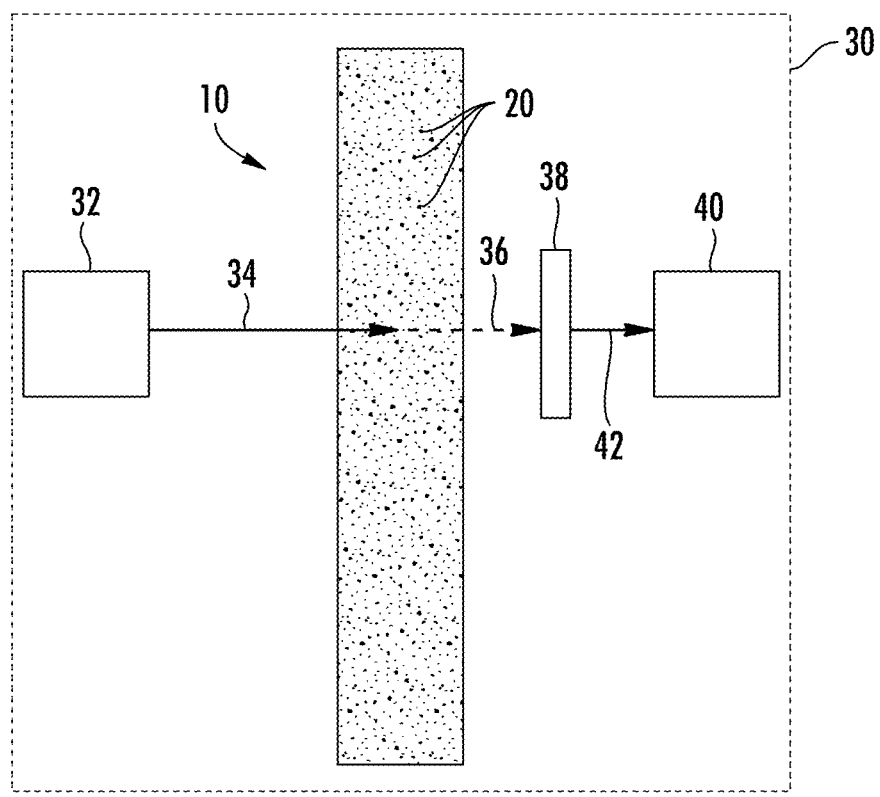

Once analyte capture device 10 has been exposed to fluid 16 for enough time (e.g., which may be predetermined based on a number of factors, including the particular environment, analyte and analyte capture rate of analyte capture device, etc.), analyte capture device 10 is removed from the environment such that exposure to analyte containing fluid 16 ceases. Then, as shown in FIG. 1D, a property of analyte 20 within analyte capture device 10 is detected within an analyte detection system 30.

In general, analyte detection system 30 includes an energy source 32 that generates energy 34 that interacts with analyte 20 generating signal 36. Signal 36 is detected by sensor 38, which communicates with a processing circuit or device, shown as processor 40, which receives and processes the signals 42 from sensor 38. In some embodiments, the property measured by analyte detection system 30 is the presence or absence of analyte 20 within analyte capture device 10. In other embodiments, the property measured by analyte detection system 30 is the quantity of analyte 20 within analyte capture device 10.

In specific embodiments, energy source 32 may be a light source, a UV source, an IR source, a laser light source, etc. In specific embodiments, sensor 38 may include charge coupled devices (CCDs), photodiodes, photodiode arrays, photoconductors, phototransistors, photomultiplier tubes, etc. or any other sensing device capable of generating an output signal 42 based on interaction with signal 36. In general, processor 40 is configured with hardware and/or software for receiving signals 42 and for processing signals 42 to determine one or more characteristic (e.g., presences, amount, concentration, type, etc.) of analyte 20. In various embodiments, processor 40 can include a wide range of hardware and/or software that receives and processes signals 42. In various embodiments, processor 40 may be a processor of a general purpose computing device, such as a smartphone, tablet, smartwatch, smart glasses, laptop computer, desktop computer, etc. In other embodiments, processor 40 may be the dedicated processor (e.g., a dedicated microprocessor, a dedicated computing device, an ASIC, etc.) of a dedicated analyte detection system 30.

In various embodiments, analyte detection system 30 may be any of a variety of detection or measurement systems that detect or measure analyte 20 within analyte capture device 10. In various embodiments, analyte detection system 30 is at least one of a transmission spectroscopy device, a fluorescence spectroscopy device, an adsorption spectroscopy device, a thermal desorption spectroscopy device, a mass spectroscopy device and an inductively coupled plasma mass spectrometry device. In specific embodiments, analyte detection system 30 is one of ultraviolet, visible light, near infrared, mid-infrared or infrared transmission spectroscopy device.

In one specific embodiment, analyte capture device 10 is sufficiently transparent to facilitate use of transmission optical spectroscopy or photoluminescence-based analyte detection systems 30. In such embodiments, analyte detection system 30 could be ultraviolet, visible light, near infrared, mid-infrared or infrared transmission spectroscopy. In this approach, analyte capture device 10 is a thin, flat plate of glass material that is placed in the sampling path of a spectrometer. The probe direction is thus normal to the surface of the glass material of analyte capture device 10. Acquisition of the transmission spectrum of the article would reveal the presence of the concentrated species due to absorption.

In another specific embodiment, the size of pores within the glass material of analyte capture device 10 is sufficiently below the wavelength of the optical probe. Because of this, the glass material of analyte capture device 10 behaves as a uniform optical medium, which yields low optical scattering. Thus, in a planar configuration with sufficiently flat parallel surfaces, the glass material of analyte capture device 10 can support waveguided optical modes. This configuration results in an increase in the interaction volume between the optical probe and the trapped analyte, which may further increase sensitivity. In this embodiment, the glass material of analyte capture device 10 includes a low refractive index material (cladding) on both top and bottom surface of the glass material. This could be air or a low index adhesive, for example. Additionally, the probe light is coupled into and out of the waveguide, and in specific embodiments, the probe light may be an LED/photodiode pair or a pair of grating couplers combined with a spectrophotometer and light source.

In various embodiments, analyte capture device 10 may be configured to capture and analyte detection system 30 may be designed to detect a wide variety of analytes for a wide variety of applications. In various embodiments, analyte 20 is an environmental toxin or pollutant (e.g., radon, mercury, pesticide, etc.), and analyte detection system 30 is configured to detect the presence or quantity of analyte 20 captured by analyte capture device 10. In various embodiments, analyte 20 is a pathogen (e.g., *E. coli, Salmonella, Staphylococcus* etc.), and analyte detection system 30 is configured to detect the presence or quantity of analyte 20 captured by analyte capture device 10. In various embodiments, analyte 20 is a biomarker, nucleotide, peptide or protein (e.g., a hormone, human chorionic gonadotropin for a pregnancy test, cancer indicators, etc.), and analyte detection system 30 is configured to detect the presence or quantity of analyte 20 captured by analyte capture device 10.

Figure 2:
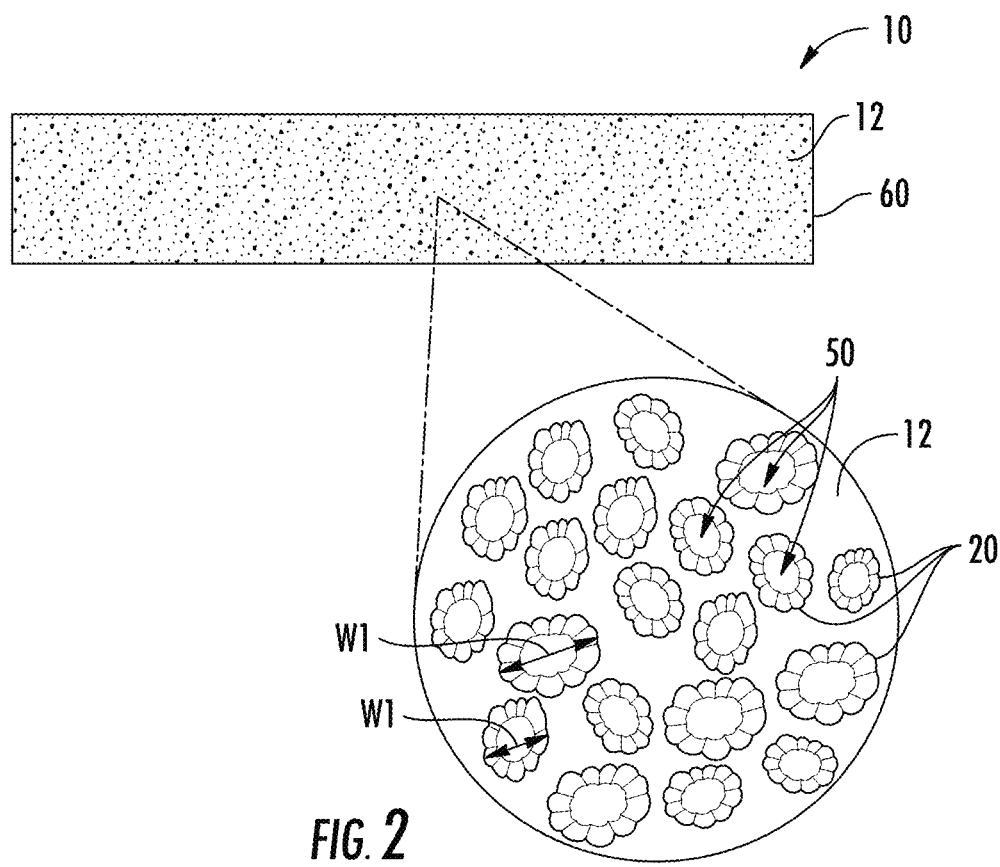
FIG. 2 shows analyte captured within the pores of a porous glass analyte capture device, according to an exemplary embodiment.
Figure 3:
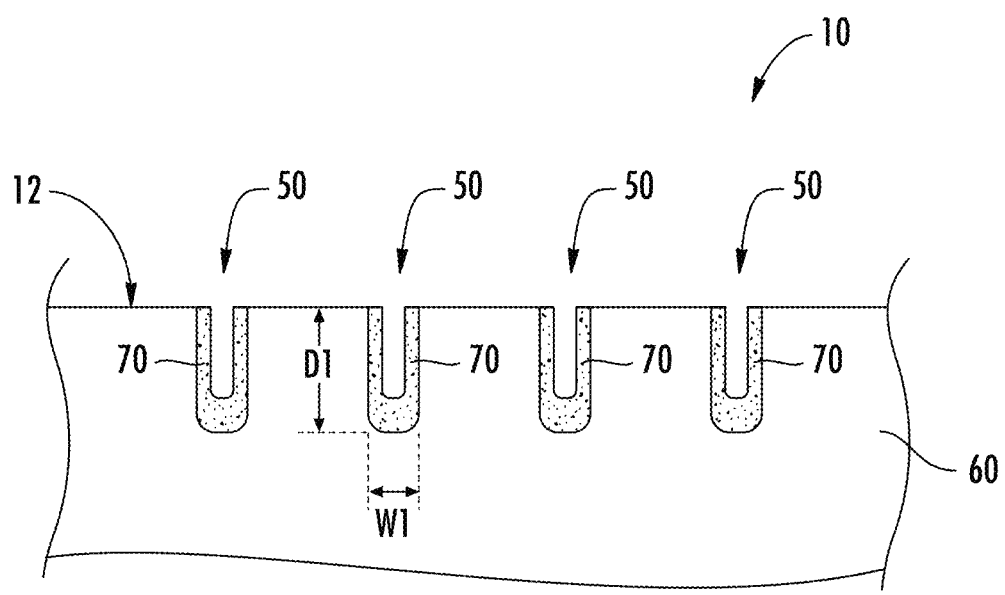
FIG. 3 is a detailed cross-sectional view of a porous area adjacent a surface of the glass analyte capture device of FIG. 2, according to an exemplary embodiment.
Figure 4:
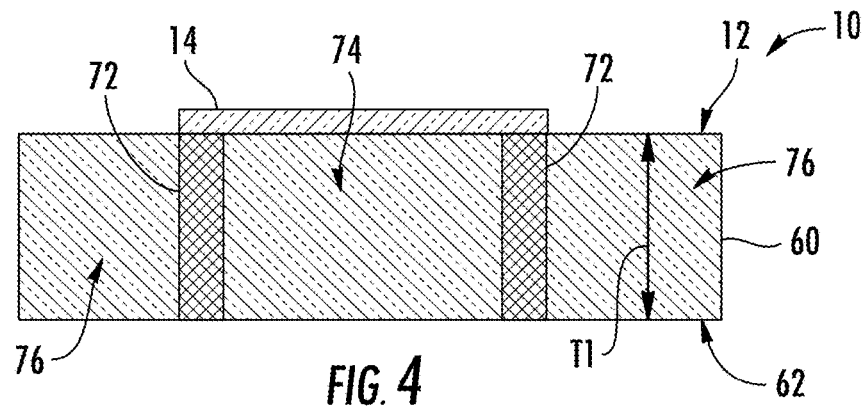
FIG. 4 is a cross-sectional view of a sealed glass analyte capture device, according to an exemplary embodiment.

Referring to FIGS. 2-4, analyte capture device 10 is shown in more detail. As shown, analyte capture device 10 is formed from a porous glass material that has a plurality of pores 50 within which analyte 20 is captured. In various embodiments, analyte capture device 10 is formed from a glass material of at least 70% silica and having a porosity of between 10% and 90%. Porosity, as used herein, should be measured via gas adsorption porosimetry for pore sizes below 50 nm and mercury porosimetry for greater than 50 nm; however, if such measurement is unavailable porosity can be measured via Brunauer-Emmett-Teller (BET) theory, transmission electron microscopy, atomic-force microscopy, scanning electron microscopy.

In specific embodiments, analyte capture device 10 is formed from a porous glass material having at least 90% silica and 2% boron trioxide, and in a specific embodiment, having about 96% silica and about 4% boron trioxide. In such embodiments, the porosity of the glass material is between 10% and 90%. In a specific embodiment, the material of analyte capture device is Vycor glass available from Corning. In other embodiments, analyte capture device 10 is formed from a nanoporous version of Gorilla Glass or a nanoporous version of EagleXG glass, both available from Corning. In such embodiments, the glass may be etched or leached to create the porosity.

As shown in FIGS. 2-4, analyte capture device 10 is formed from a glass material or sheet 60. Glass sheet 60 includes a plurality of pores 50, and in specific embodiments, at least some pores 50 form openings along surface 12. It should also be understood that while the schematic view of FIG. 3 shows pores 50 as a substantially consistent well-like structure for ease of depiction, pores 50 may be an interconnected sponge-like three dimensional network of pores located adjacent to the surfaces of glass sheet 60 and/or evenly distributed throughout the thickness of glass sheet 60.

In general, pores 50 are sized and/or positioned within glass sheet 60 in a manner that increases or improves the ability of analyte capture device 10 to absorb or otherwise capture analyte 20 within the glass material. Further, in contrast to some materials that utilize a porous coating applied to a glass or ceramic material (e.g., a porous anodic alumina coating), in specific embodiments, pores 50 provide for analyte capture in a monolithic structure without the need for a separate additional layer.

In various embodiments, pores 50 have a pore width, shown representatively as W1, and a pore depth, shown representatively as D1. In general, pore width W1 is the dimension of pores 50 within glass sheet 60 measured in the direction perpendicular to the thickness of glass sheet 60 for the pores 50, and in embodiments where pores 50 are substantially circular in cross-section, W1 represents a diameter. In some embodiments, W1 represents the largest dimension of pores 50 within glass sheet 60. In various embodiments, the average of W1 of all pores within glass sheet 60 or within a region of glass sheet 60 is less than 100 nm, and more specifically is greater than 1 nm and less than 30 nm. In the case of pores 50 located along or adjacent surface 12, a pore depth D1 can be measured that is the pore dimension parallel to the thickness of glass sheet 60. In various embodiments, the average of D1 of all pores within glass sheet 60 or within a region of glass sheet 60 is between 10 nm and 10 µm.

In various embodiments, pore width and/or pore depth as discussed herein may be measured via a variety of standard pore methods. For example, pore width and pore depth as discussed herein may be measured using Brunauer-Emmett-Teller (BET) theory, transmission electron microscopy, atomic-force microscopy, scanning electron microscopy, etc.

In various embodiments, pores 50 increase the surface area of surface 12 as compared to a planar nonporous surface which in turn increases the ability of glass sheet 60 to absorb the desired analyte. In various embodiments, the area of surface 12 is 2× greater, 10× greater, or 100× greater than a nonporous planar glass surface having the same outer dimensions as glass sheet 60.

Glass sheet 60 and/or pores 50 may be formed from a variety of processes or techniques. In specific embodiments, including embodiments where glass sheet 60 is Vycor glass, pores 50 are formed via a phase separation process combined with selective etching. In a specific embodiment, the phase separation process as well as subsequent heat treatments of the porous Vycor body can be used to tune pore size and distribution. In other embodiments, pores 50 may be formed through any suitable process including laser etching, photolithography, e-beam lithography, self-assembly of an etch mask, nanoimprint lithography, use of block copolymer masks, wet chemical etching/leaching, ion-exchange induced phase separation, etc. In some embodiments, glass sheet 60 may be fabricated via a technique that results in porous glass and in such embodiments, pores 50 are not formed via a secondary formation step.

Referring to FIG. 4, glass sheet 60 includes a thickness T1 between outer surface 12 and lower surface 62. In particular embodiments, T1 is between 20 micrometers and 4 millimeters, and specifically is between 20 micrometers and 2 millimeters. In the embodiments shown, surface 12 and surface 62 are substantially planar (except for pores located at surfaces 12 and/or 62 as discussed herein), and in other embodiments, surface 12 and/or surface 62 may be convex or concave curved surfaces, may be angled relative to each other or may include other complex curves or shapes.

In addition to having porosity and/or chemical composition that allows for analyte capture, the glass material 60 of analyte capture device 10 may also have other characteristics that allow it to be used within analyte detection system. For example, glass sheet 60 may have a high level of transparency allowing for use in various spectrographic applications. In specific embodiments, glass material 60 has greater than 50% transparency at wavelengths from 250 nm to 2500 nm, and specifically greater than 70% transparency at wavelengths from 250 nm to 2500 nm. In a specific embodiment, Vycor glass has been determined to exhibit greater than 70% transparency from 250 nm to 2500 nm. In addition, the glass may be both mechanically and chemically stable.

In various embodiments, glass sheet 60 may include an analyte capture material 70 supported within pores 50. In general, analyte capture material 70 is a material that has a higher affinity for analyte 20 than for other materials in the environment or in fluid 16 such that analyte capture material 70 facilitates adhesion, absorption or retention of analyte 20 within in analyte capture device 10. In various embodiments, analyte capture material 70 is a chemical compound supported within pores 50 that captures or binds analyte 20 via a variety of suitable mechanisms, such as through electrostatic interactions, covalent bonding, chelation, physisorption and chemisorption.

As will be understood, analyte capture material 70 is selected based on a property that differentially allows analyte capture material 70 to bind the analyte of interest. For example, if the analyte is a non-polar molecule such as pathogens suspended in a polar solvent like water, analyte capture material 70 may be a hydrophobic/oleophilic material which would lead to strong enrichment of the pathogens in the volume of pores 50.

Referring to FIG. 4, cover 14 is shown coupled to glass sheet 60. In this arrangement, cover 14 is hermetically sealed to outer surface 12 and hermetically seals some or all of pores 50 (shown in FIG. 3) of glass sheet 60 from exposure prior to use. Cover 14 can be any suitable material that is impermeable to analyte 20 prior to being opened. As noted above regarding FIG. 1, cover 14 is openable or removable to expose pores 50 to the environment during use.

In a particular embodiment, glass sheet 60 is formed from a porous glass material that includes pores evenly distributed throughout the material (e.g., fully leached Vycor glass). In such embodiments, analyte capture device 10 includes a perimeter seal 72. Perimeter seal 72 is a hermetic sealing structure that provides an impermeable barrier to analyte 20. In this embodiment, perimeter seal 72 seals an analyte capture area 74 from adjacent areas 76 of glass sheet 60. As can be seen, adjacent areas 76 are not covered by cover 14 and therefore may absorb analyte material prior to analyte capture device being used. In such embodiments, perimeter seal 72 isolates analyte capture area 74 from adjacent areas 76 by blocking or preventing migration of analyte from adjacent areas 76 into analyte capture area 74. In a specific embodiment, perimeter seal 72 is a region of densified (e.g., through laser melting) glass material.

In some embodiments, following exposure of analyte capture device 10 to the analyte containing material or environment, cover 14 may be reapplied to glass sheet 60 to limit further analyte absorption. It should be understood that while cover 14 is shown having a smaller size than glass sheet 60, cover 14 may be any suitable sealing structure or packaging for hermetically sealing analyte capture device 10 from the environment. In some embodiments, cover 14 may completely surround analyte capture device 10.

Analyte Capture Material Examples

Referring to FIGS. 5-8B, various embodiments of analyte capture device 10 configured to capture particular analyte materials and including various analyte capture materials 70 within pores 50 are shown and described. In particular embodiments, analyte capture material 70 may be a highly selective concentrator for specific analytes of interest being targeted. Particularly in those cases where the capture and subsequent analysis of specific materials/contaminants is desired, glass sheet 60 may be converted to a selective concentrator by addition of a specific analyte capture material 70 to porous surface of glass sheet 60.

For example, pores 50 on the surface of glass sheet 60 may be tailored to include chemically reactive organic/inorganic molecules or macromolecular arrays that attract and trap specific analytes of interest. In specific embodiments, analyte capture material 70 may be configured to utilize one or more of the following attraction methods for differentially attracting the desired analyte: (i) non-covalent and/or electrostatic interactions, (ii) covalent-bond reactivity, or (iii) site-specific host-guest interactions.

Figure 5:
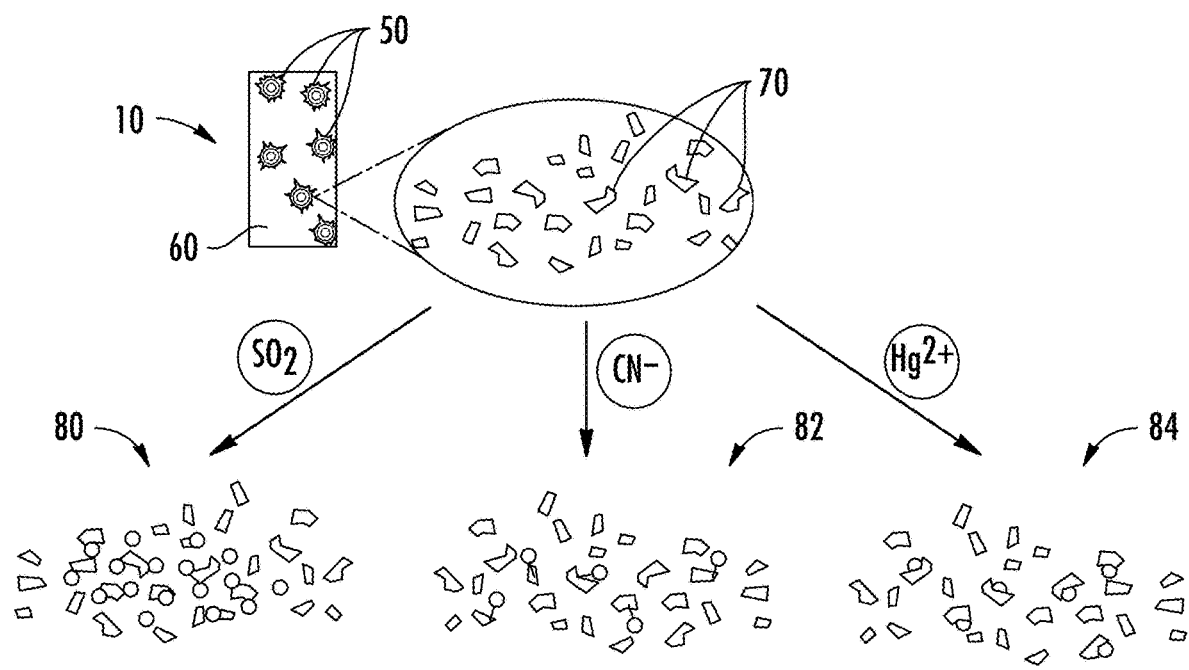
FIG. 5 is a schematic view showing an analyte capture material within pores of a glass analyte capture device, according to an exemplary embodiment.

In some embodiments, surface functionalization of glass sheet 60 may allow for the desired analyte capture material to be effectively impregnated within the porous glass matrix. FIG. 5 provides several examples of analyte capture materials 70 that may be used with glass sheet 60 of analyte capture device 10. In one embodiment, as shown at 80 in FIG. 5, analyte capture device 10 is configured for capture of sulfur dioxide ($SO_2$) from air sources. In this embodiment, analyte capture material 70 captures $SO_2$ via non-covalent chemisorption interactions.

Figure 6:
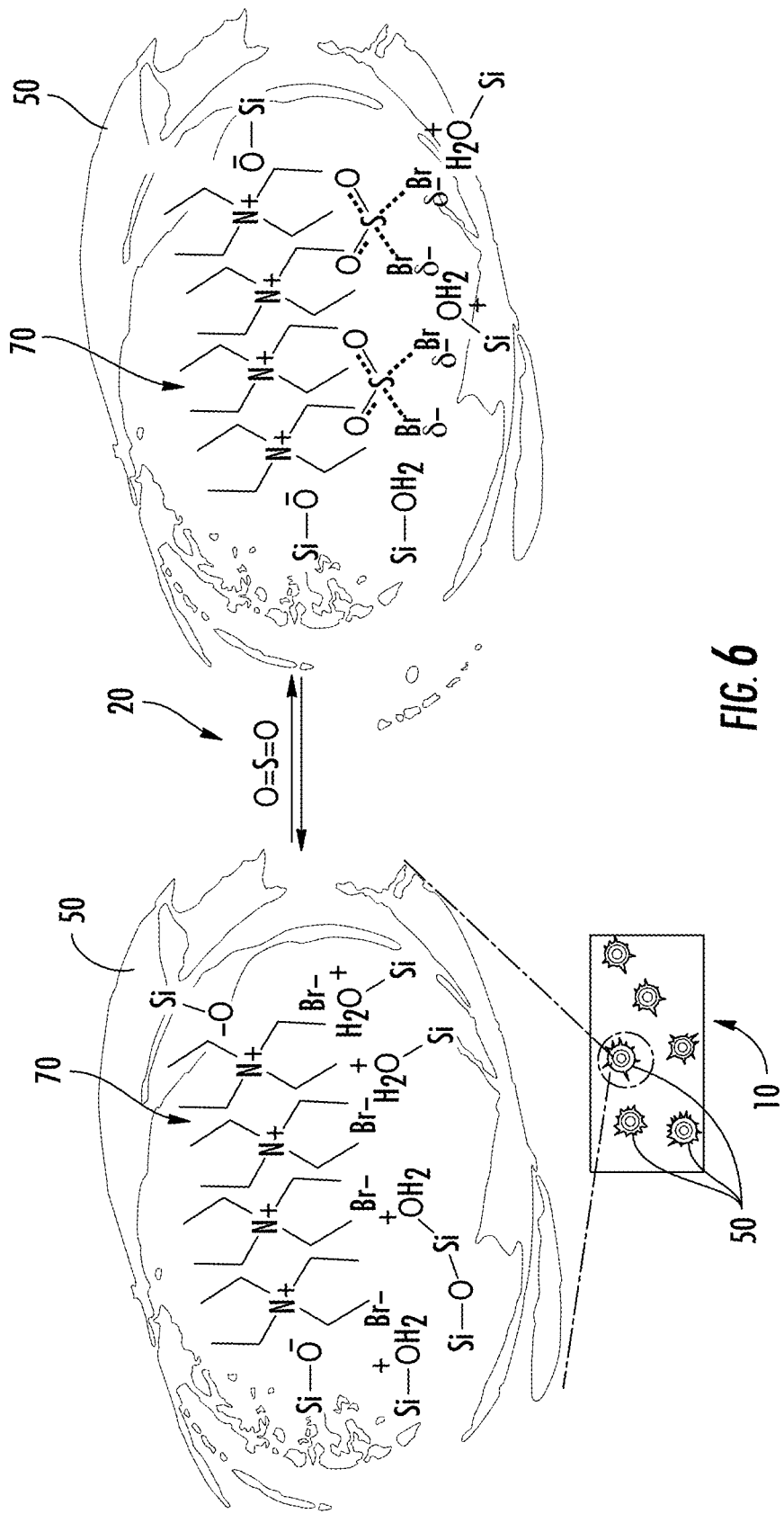
FIG. 6 is a schematic view showing an analyte capture material within pores of a glass analyte capture device, according to another exemplary embodiment.

Referring to FIG. 6, details of analyte capture device 10 configured for $SO_2$ capture is shown according to an exemplary embodiment. The uptake of sulfur dioxide gas by the glass material of analyte capture device 10 can be achieved through a chemical adsorption process (chemisorption) wherein the adsorbate molecules would react directly with the glass surface interface. In this embodiment, to render the glass surface $SO_2$-reactive, the porous glass material of analyte capture device 10 is impregnated with quaternary ammonium salts of the general formulation $R_4NX$ (R=$CH_3$, $C_2H_5$; X=I, Br).

As shown in FIG. 6, the ammonium salts can effectively trap the $SO_2$ species through a charge-transfer interaction between the salt halide ions and the S—O bonds, yielding a new molecular framework $[R_4NX.SO_2]_n$. Generation of $[R_4NX.SO_2]_n$ could proceed at ambient temperature while the absorbed gas is readily desorbed from pores 50 by applying either a dynamic vacuum or modest heat. The $SO_2$ desorption process can be coupled with direct-reading instrumental methods for detection and quantification of trace air pollutants (e.g. UV fluorescence, differential optical absorption spectroscopy). Alternatively, suitable spectroscopic measurements may be realized directly on the $SO_2$-absorbed surface of the glass sample (e.g. Raman spectroscopy). Finally, the introduction of sorbent material ($R_4NX$) into the pores may be achieved with high charge-density glass samples, accessed at high pH, which is known to result in enhanced adsorption of ionic ammonium salts. Altogether, the $SO_2$ glass concentrator exemplifies a non-covalent adhesion strategy for selective accumulation and/or extraction of gas-phase air pollutants.

In another embodiment, as shown at 82 in FIG. 5, analyte capture device 10 is configured for capture of cyanide anions ($CN^-$). In this embodiment, analyte capture material 70 captures cyanide anions via formation of covalent bonds.

Figure 7A:
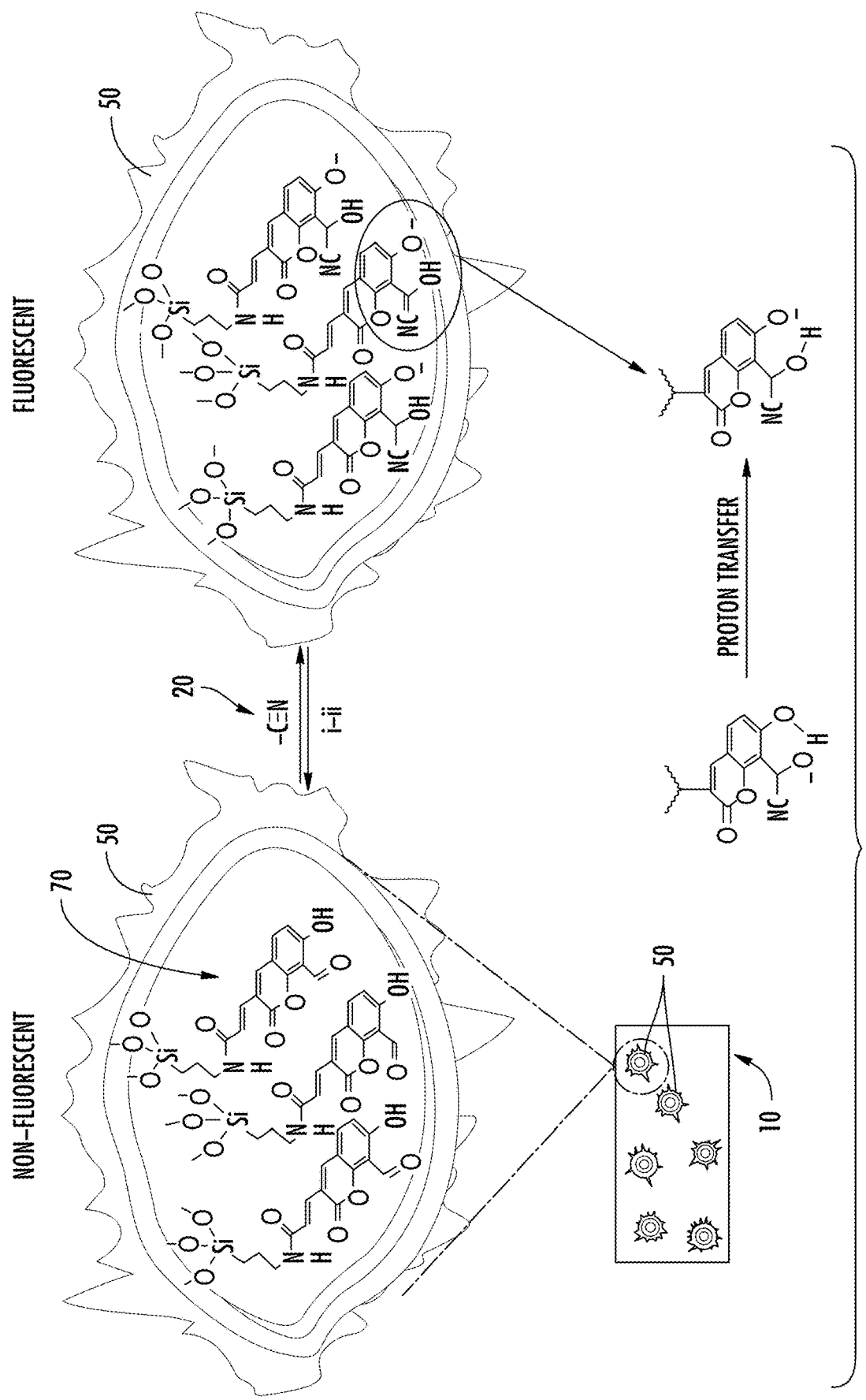
FIGS. 7A and 7B are schematic views showing an analyte capture material within pores of a glass analyte capture device, according to other exemplary embodiments.
Figure 7B:
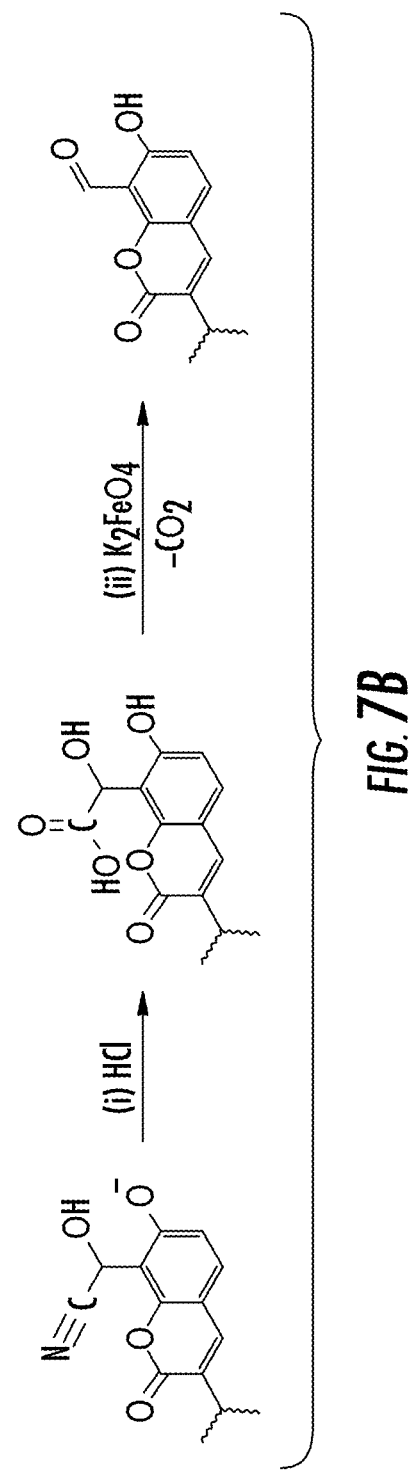

Referring to FIGS. 7A and 7B, details of analyte capture device 10 configured for cyanide anions capture is shown according to an exemplary embodiment. In this embodiment, analyte capture device 10 configured for the extraction of cyanide provides an example of selective removal of charged pollutants from an aqueous environment. In this embodiment, $CN^-$ sensing chemistry is designed to take place at the solid-liquid interface via direct immersion of analyte capture device 10 into aqueous media. In contrast to the non-covalent mode of $SO_2$ adhesion, the accumulation of $CN^-$ ions within the glass framework of analyte capture device 10 utilizes a carbon-carbon bond forming reaction.

As shown in FIG. 7A, glass pores 50 support covalently immobilized organic dyes (coumarins), with each individual dye bearing a chemically reactive aldehyde group (CHO) to be used as a trapping agent for the cyanide ions. Specifically, the individual aldehyde moieties are amenable toward nucleophilic attack by the cyanide anion, resulting in new C—C bonds. Hence on exposure of the coumarin species to cyanide, new CN-adducts can be derived with strongly fluorescent characteristics ($\lambda_{em}$~450 nm).

Given that the cyanide-induced emission would be expected to occur within the porous glass interface, the glass material of analyte capture device 10 itself could serve as an optical probe for the quantification of $CN^-$. In this embodiment, inherent light-scattering patterns of the glass material are minimized, and the CN-adducts are sufficiently stable in the solid state. The CN-adducts are believed to be effectively stabilized through an intramolecular proton transfer between the phenol hydrogen (OH) and the negative charge introduced on the dye molecule from the cyanide ion attack (FIG. 7A).

In a specific embodiment, the acquired $CN^-$ ions are removed to render analyte capture device 10 reusable. In a specific embodiment, the concentrating capability of analyte capture device 10 is regenerated through suitable chemical manipulations. For example, as shown in FIG. 7B, the original aldehyde groups can be restored on sequential treatment of analyte capture device 10 with a strong acid (e.g. HCl) and a strong oxidant (e.g. $K_2FeO_4$). The strong acid promotes hydrolysis of the nitrile groups (CN) to carboxylic acids, and the strong oxidant removes the carboxylic acids via oxidative loss of carbon dioxide.

In yet another embodiment, as shown at 84 in FIG. 5, analyte capture device 10 is configured as a chelating agent for removal of mercury ions ($Hg^{2+}$) from aqueous environments. In this embodiment, analyte capture material 70 captures mercury ions via chelation.

Figure 8A:
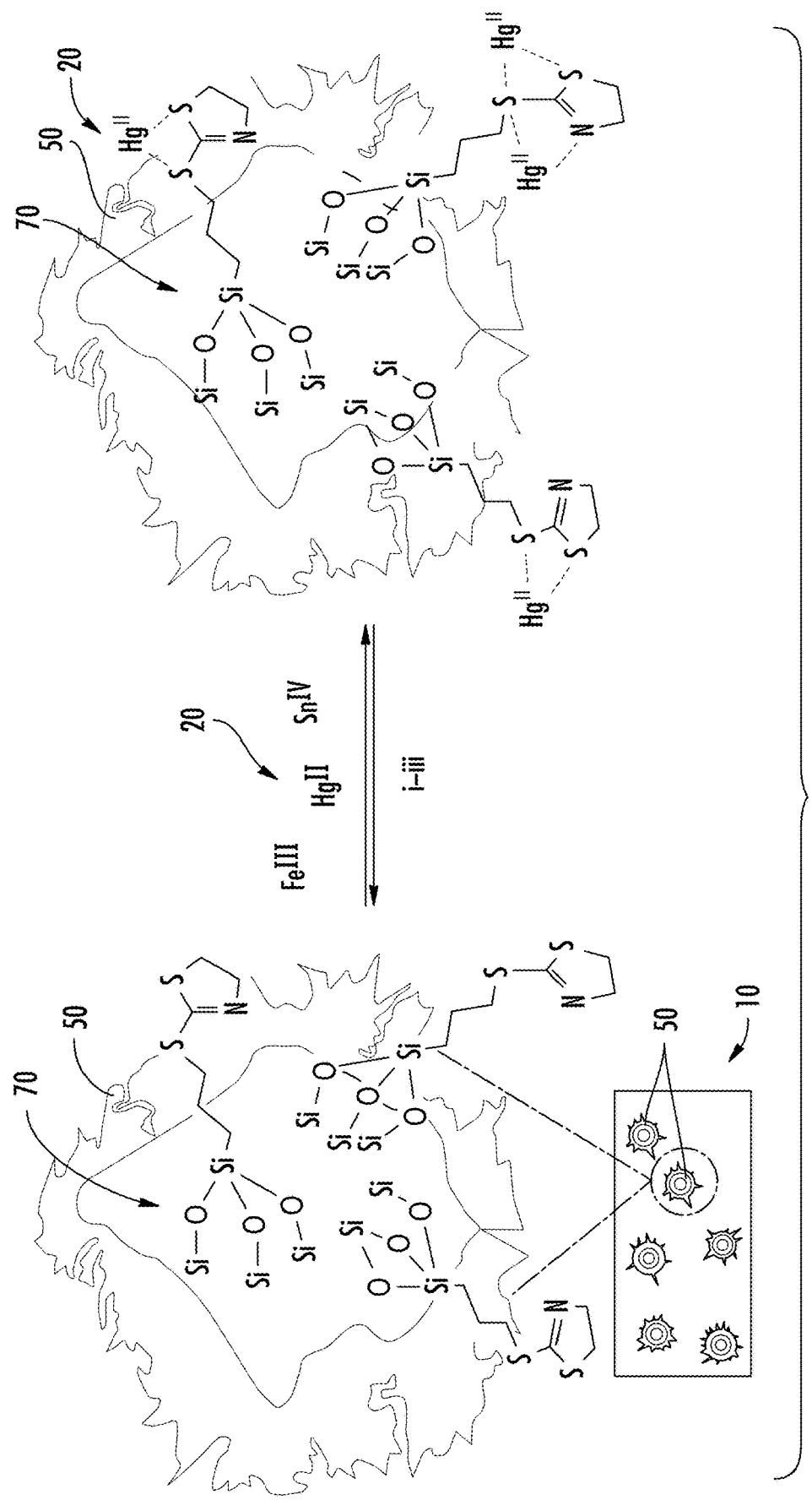
FIGS. 8A and 8B are schematic views showing an analyte capture material within pores of a glass analyte capture device, according to other exemplary embodiments.
Figure 8B:
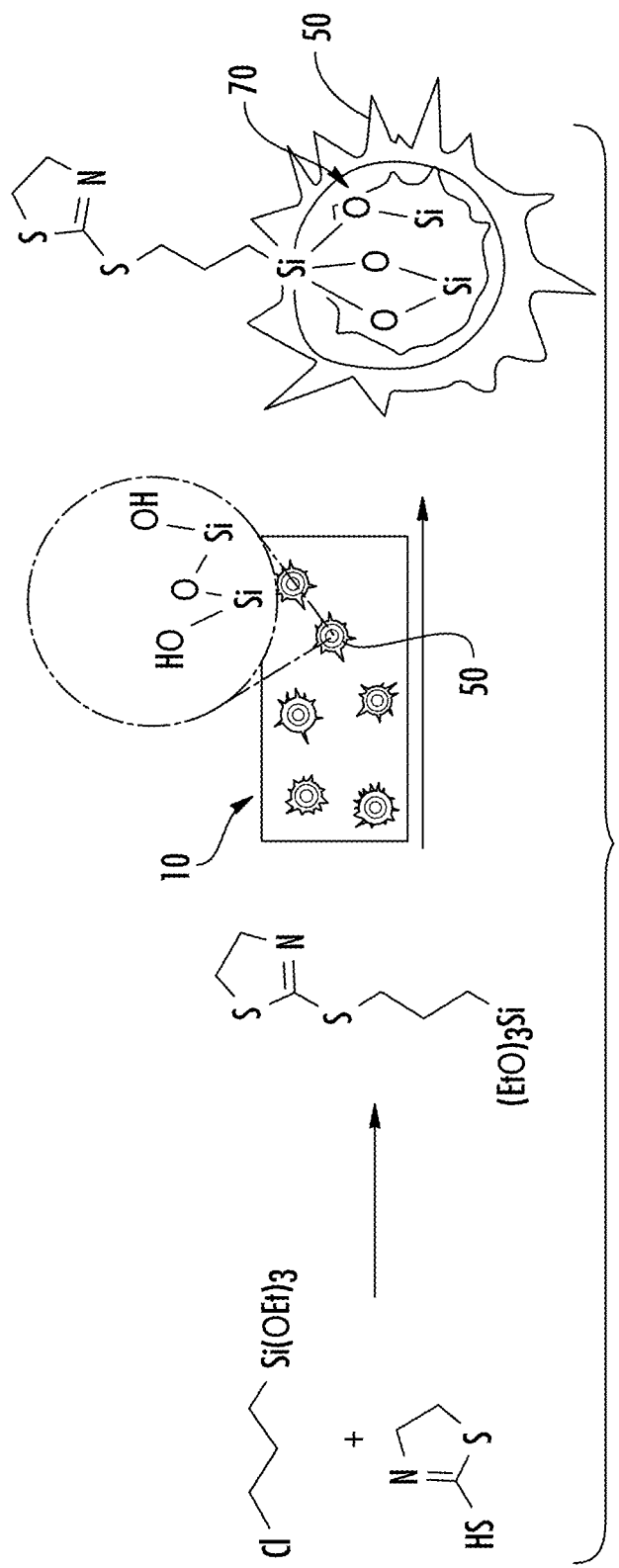

Referring to FIGS. 8A and 8B, details of analyte capture device 10 configured for mercury ion capture are shown according to an exemplary embodiment. This embodiment provides an example of analyte capture device 10 including a chelating agent supported by glass pores 50 to provide capture of heavy metal ions from aqueous solutions. A chelating agent is generally defined as a small organic molecule that binds tightly to metal ions.

FIG. 8A illustrates the concept of metal chelators in the context of mercury cation removal. Pores 50 of analyte capture device 10 are shown as supporting 2-mercaptothiazoline chelators (ligands) that have intrinsic proclivity to attract and bind $Hg^{2+}$ ions. In particular, the sulfur donor atoms of the ligand show a thermodynamic preference for binding soft metal acids such as mercury(II) to give rise to stable coordination metal complexes. The metal-complex stability is further enhanced through more than one sulfur atom being able to donate electronic density to the metal ion (multidentate coordination mode). In this manner, the function of the 2-mercaptothiazoline ligand is to create selective recognition sites within the surface of the concentrator so that analyte capture device 10 can capture toxic, soft metal ions (e.g. $Hg^{2+}$, $Cd^{2+}$) yet leave behind hard metal ions (e.g. $Fe^{3+}$, $Sn^{4+}$, $Mn^{2+}$) in the sample fluid/environment.

In such embodiments, the chelation method is designed such that the metal-extraction step will proceed at the solid-liquid interface. For this reason, covalent surface chemistry can be deployed in order to permanently append the chelating agent of choice to the glass surface of analyte capture device 10 as well as to properly orient the chelating component of the molecule, in a directional manner and away from the inner pores, thus increasing its overall accessibility toward metal-centered interactions. As shown in FIG. 8B, the mercury-specific chelator can be introduced into the pores by a two-stage process. First, the silylating agent is prepared by reaction of 3-chloropropylsilane with mercaptothiazoline (the molecule that binds $Hg^{2+}$). Second, the resulting compound is allowed to react with an activated glass surface, rich in Si—OH groups, leading to covalent immobilization of the chelating agent. Following complexation of the metal ions, the analyte detection process may be achieved by subjecting analyte capture device 10 to either direct surface-based analysis methods (e.g. Raman spectroscopy if applicable) or solid-state desorption techniques for independent analysis. In the latter case, the sequestered metal ions can be removed by several surface manipulation strategies including thermo-desorption, pH-adjustments, or suitable ligand-exchange reactions.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that any particular order be inferred. In addition, as used herein, the article "a" is intended to include one or more components or elements, and is not intended to be construed as meaning only one.

It will be apparent to those skilled in the art that various modifications and variations can be made without departing from the spirit or scope of the disclosed embodiments. Since modifications, combinations, sub-combinations and variations of the disclosed embodiments incorporating the spirit and substance of the embodiments may occur to persons skilled in the art, the disclosed embodiments should be construed to include everything within the scope of the appended claims and their equivalents.

What is claimed is:

1. A method of detecting a low concentration analyte in an environment, the method comprising:
    exposing an analyte capture device to an environment containing an analyte, the analyte capture device comprising:
        a glass material;
        an outer surface defined by the glass material;
        a plurality of pores formed in the glass material along at least a portion of the outer surface such that the glass material has a porosity of at least 10%;
        wherein the plurality of pores define an analyte capture area; and
        wherein the analyte capture area is surrounded by a perimeter seal comprising a region of densified glass material;
    continuing exposure of the analyte capture device to the environment for a period of time such that the analyte is captured within the analyte capture area, wherein a concentration of the analyte within the glass material is greater than a concentration of the analyte within the environment;
    removing the analyte capture device from the environment by placing a cover over the perimeter seal to create a hermetic seal that limits further analyte absorption; and
    detecting a property of the analyte captured by the analyte capture device via an analyte detection system.

2. The method of claim 1, wherein, prior to the step of exposing, the method further comprises removing a hermetic seal between the cover and the perimeter seal that blocks the analyte capture area of the analyte capture device, wherein exposing the analyte capture device to the environment comprises passing a fluid containing the analyte across the outer surface and across the plurality of pores.

3. The method of claim 1, wherein the plurality of pores have an average pore width that is less than 100 nm.

4. The method of claim 3, wherein the outer surface is a substantially planar surface.

5. The method of claim 4, wherein the average pore width is greater than 1 nm and less than 30 nm, wherein the pores increase the area of the outer surface of the glass material such that the area of the outer surface is at least 10 times an area defined by a perimeter of the outer surface.

6. The method of claim 1, wherein the glass material has a thickness between 20 μm and 4 mm, wherein the plurality of pores are evenly distributed throughout the thickness of the glass sheet.

7. The method of claim 1, wherein the glass material comprises at least 90% silica and at least 2% boron trioxide.

8. The method of claim 1, wherein the analyte capture device further comprises an analyte capture material supported within the plurality of pores, wherein the analyte capture material has a higher affinity for the analyte than for other materials in the environment.

9. The method of claim 8, wherein the analyte capture material captures the analyte within the pores via at least one of electrostatic interactions, covalent bonding, chelation, physisorption and chemisorption.

10. The method of claim 8, wherein the analyte capture material comprises quaternary ammonium salts of the general formulation $R_4NX$, wherein R=$CH_3$, $C_2H_5$; X=I, Br, and wherein the analyte is $SO_2$.

11. The method of claim 8, wherein the analyte capture material comprises a reactive aldehyde group and wherein the analyte is cyanide anions.

12. The method of claim 11, wherein the method further comprises the step of sequentially treating the analyte capture device with a strong acid and a strong oxidant in order to restore the reactive aldehyde groups after exposure to the cyanide anions.

13. The method of claim 8, wherein the analyte capture material comprises a chelating agent and wherein the analyte is mercury ions.

14. The method of claim 13, wherein the chelating agent comprises 2-mercaptothiazoline chelators.

15. The method of claim 13, further comprising the step of introducing the chelating agent to the plurality of pores by preparing a silylating agent and reacting the silylating agent with an activated glass surface.

16. The method of claim 15, wherein preparing the silylating agent comprises reacting 3-chloropropylsilane with mercaptothiazoline.

17. The method of claim 16, wherein the activated glass surface is rich in Si—OH groups.

18. The method of claim 8, wherein the analyte capture material comprises a hydrophobic or oleophilic material and wherein the analyte comprises a non-polar molecule suspended in a polar solvent.

19. The method of claim 1, wherein the analyte detection system utilizes at least one of transmission spectroscopy, fluorescence spectroscopy, adsorption spectroscopy, thermal desorption spectroscopy and mass spectroscopy.

20. The method of claim 1, wherein the plurality of pores are formed through at least one of laser etching, photolithography, e-beam lithography, self-assembly of an etch mask, nanoimprint lithography, use of block copolymer masks, wet chemical etching or leaching, or ion-exchange induced phase separation.

* * * * *